United States Patent [19]

Shinohara et al.

[11] 4,198,284
[45] Apr. 15, 1980

[54] ELECTROPHORETIC APPARATUS

[75] Inventors: Toshio Shinohara, Chofu; Ryo Fujimori, Hachiouji, both of Japan

[73] Assignee: Olympus Optical Co., Ltd., Tokyo, Japan

[21] Appl. No.: 32,222

[22] Filed: Apr. 23, 1979

[30] Foreign Application Priority Data

Apr. 27, 1978 [JP] Japan .............................. 53-55250[U]
Apr. 27, 1978 [JP] Japan .............................. 53-55251[U]

[51] Int. Cl.² ...................... G01N 27/26; G01N 27/28
[52] U.S. Cl. ............................ 204/299 R; 204/180 S
[58] Field of Search ........... 204/180 R, 180 S, 180 G, 204/299, 300

[56] References Cited

U.S. PATENT DOCUMENTS

| 3,133,009 | 5/1964 | Natelson | 204/299 R |
| 3,764,513 | 10/1973 | Saravis | 204/299 R |
| 3,896,021 | 7/1975 | Fosslien | 204/299R |
| 4,059,501 | 11/1977 | Strickler | 204/299 R |

*Primary Examiner*—Arthur C. Prescott
*Attorney, Agent, or Firm*—Cushman, Darby & Cushman

[57] ABSTRACT

An electrophoretic apparatus comprising a pair of endless belts for conveying a film into and out of the apparatus, filter paper supports on which edge portions of filter paper sheets are placed and filter paper retainers arranged above the filter paper supports. The electrophoretic apparatus is arranged that, after the film is conveyed into the apparatus by means of endless belts, the film is moved upward by moving the filter paper supports upward and thereby holding the edge portions of film between the filter paper supports and filter paper retainers, edge portions of film are pulled in the direction opposite to each other and, then, the film is energized, the electrophoretic apparatus being thereby arranged that the film is energized in the state that it is free from slack so that favorable fractionated patters are obtained.

6 Claims, 8 Drawing Figures

ELECTROPHORETIC APPARATUS

BACKGROUND OF THE INVENTION (a) Field of the invention

The present invention relates to an electrophoretic apparatus and, more particularly, to an electrophoretic apparatus for an automatic electrophoretic system to be used for analysis of blood serum proteins etc.

(b) Description of the prior art

For analysis of blood serum proteins in clinical study and the like, electrophoresis is usually adopted. To analyze blood serum proteins by electrophoresis, blood serum is applied onto a film made of cellulose acetate paper or the like (hereinafter referred to as film) and is subjected to electrophoresis in an electrophoretic apparatus. However, such processes required for analysis are carried out by handwork. Therefore, it is impossible to carry out the analysis efficiently. Moreover, to analyze many specimens of blood serum, it takes an extremely long time.

To eliminate the above-mentioned disadvantages of known electrophoresis, an automatic system is developed by automatizing all processes required for electrophoresis and arranging to perform all of those processes continuously. In the above-mentioned system, the electrophoretic apparatus in which the specimens are actually subjected to electrophoresis is arranged as follows. That is, a film onto which the blood serum specimens are applied is fed into the electrophoretic apparatus by means of a pair of endless belts arranged in the electrophoretic apparatus, stopped at a pre-determined position for the purpose of energizing the film and, then energized for a pre-determined time by keeping it stopped. After being energized, the film is transferred to the next process by starting the belts again. Now, detailed construction of the above-mentioned electrophoretic apparatus is described below referring to FIGS. 1 through 3. In these figures, numeral 1 designates a main body of electrophoretic apparatus, numeral 2 designates a lid and numeral 3 designates two pairs of rollers out of which one pair are arranged near an entrance 1a through which the film is fed into the main body 1 and the other pair are arranged near an exit 1b through which the film goes out of the main body 1 after electrophoresis. Numeral 4 designates a pair of endless belts applied to the rollers 3. Numeral 5 designates a motor which rotates the rollers 3 and thereby drives the endless belts 4. Therefore, when the film is inserted through the entrance 1a, the film is fed into the main body 1 by the belts 4 and, after being energized by the means to be described later, it is delivered out of the main body 1 through the exit 1b also by the belts 4. Numeral 6 designates a pair of partition walls fixed to the main body 1 or formed integrally with the main body 1. In trough portions 1c and 1d partitioned by the partition walls 6, buffer solution 7 is to be filled. Numeral 8 designates a pair of long board-like filter paper supports arranged on the right and left. Top surfaces of filter paper supports 8 are sloped as it is evident from their sections shown in FIG. 2. Numeral 10 designates a pair of supporting arms. At both ends of each supporting arm 10, leaf springs 11 are fixed and hold screws 9 which are respectively fixed to the filter paper supports 8. Thus, the filter paper supports 8 are dismountably supported. Numeral 12 designates a pair of supporting rods which support the supporting arms 10 and are mounted to the main body 1 so that the supporting rods 12 can be moved in vertical direction. Numeral 13 designates a pair of cams fixed to a shaft 14 and positioned just below the supporting rods 12. By roration of cams 13, the supporting rods 12 are moved upward and downward and the filter paper supports 8 are thereby moved upward and downward. Numeral 15 designates two sheets of filter paper. Each sheet of filter paper 15 is arranged that its one edge portion rests on the top surface of one of filter paper supports 8 and the other edge portion is dipped into buffer solution 7. Numeral 16 designates a pair of long board-like filter paper retainers respectively arranged above the filter paper supports 8. By inserting pins 16a fixed to each filter paper retainer 16 into slots 1e which are formed in the main body 1, each filter paper retainer 16 is held at a pre-determined height shown in FIG. 2. Numeral 17 designates a pair of wires stretched above the belts 4 by means of fixtures 18 fixed to the filter paper supports 8. Numeral 19 designates doors which are slidable in vertical direction for the purpose of opening and closing the entrance 1a and exit 1b. Numeral 20 designates crank mechanisms for moving the doors 19 upward and downward being operated by rotation of shaft 14.

Now, operation of the above-mentioned known electrophoretic apparatus is briefly described below. At first, the film to which blood serum specimens are applied is inserted through the entrance 1a by a suitable means. When the motor 5 is started at the same time in order to drive the endless belts 4, the film is fed into the main body 1 by the endless belts 4. When the film comes to a pre-determined position, the endless belts are stopped and, then, the shaft 14 are rotated by a suitable drive mechanism. Thus, the cams 13 fixed to the shaft 14 are rotated, the filter paper supports 8 are pushed up as explained before and the top surfaces of filter paper supports are pushed against the bottom surfaces of filter paper retainers 16. When, as shown in FIG. 2, it is so arranged that the distance between both endless belts 4 is smaller than the width of film 30 to which the blood serum specimens are applied, both edges of film 30 which is brought to the predetermined position on the endless belts 4 are projecting to the outside of endless belts 4. Therefore, when the filter paper supports are moved upward as described in the above, the film 30 also moves upward at the same time parting from the top surfaces of belts and is held between the filter paper supports 8 and filter paper retainers 16 together with the two sheets of filter paper 15. When the electrodes which are arranged in the buffer solution 7 but not illustrated are energized in the above state, the film 30 is energized through the two sheets of filter paper 15 for which one edge of each filter paper is dipped in the buffer solution 7.

On the other hand, when the shaft 14 is rotated, the doors 19 are moved upward through the crank mechanisms 20. Therefore, the entrance 1a and exit 1b are closed at the same time as the filter paper supports 8 are moved upward by rotation of cams 13 as described before. When the cams 13 are rotated and crank mechanisms are operated again after energizing for a pre-determined time, the filter paper supports 8 and doors 19 move downward. When the filter paper supports 8 move downward at that time, the wires 17 stretched across the fixtures 18, which are fixed to the filter paper supports 8, also move downward. Therefore, even if the film sticks to the filter paper retainers 16, it is moved downward without fail by means of the wires.

The film which is subjected to electrophoresis is thus placed on the endless belts 4 again. When the belts are driven by starting the motor at that time, the film is delivered to the outside through the exis 1b and is transferred to the next process.

The known electrophoretic apparatus described in the above has the following disadvantages. That is, when the film is conveyed to the pre-determined position for energization in the electrophoretic apparatus by means of endless belts, the middle portion of film which locates between the belts hangs slack and the film is energized in that state. Therefore, it is not possible to obtain favourable fractionated patterns. Moreover, as the filter paper retainers 16 have flat board-like shape, poor contact occurs between the film and filter paper when the edges of film are held between the filter paper supports 8 and filter paper retainers 16 unless it is so arranged that the respective contacting surfaces of filter paper supports 8 and filter paper retainers 16 have very favourable flatness so that there remains no such portion where those surfaces do not satisfactorily contact each other. Besides, when the filter paper supports 8 are moved downward in order to return the film onto the endless belts after energization, the film sometimes sticks to the filter paper retainers 16 and does not comes down onto the belts. In the known apparatus, it is therefore necessary to stretch the wires 17 and to separate the film from the filter paper retainers 16 by those wires when the filter paper supports 8 move downward. As, however, it is impossible to make the distance between the belts 4 and wires 17 large, the film sometimes gets jammed between the belts and wires when it is being conveyed by the belts.

SUMMARY OF THE INVENTION

It is therefore a primary object of the present invention to provide an electrophoretic apparatus for an automatic electrophoretic system comprising endless belts for conveying a film into and out of the apparatus, filter paper supports on which edge portions of filter paper sheets are placed and filter paper retainers arranged above the filter paper supports, said electrophoretic apparatus being arranged that the film is held between the filter paper supports and filter paper retainers after the film is conveyed by the endless belts into the space between the filter paper supports and filter paper retainers, the film is then moved upward so that its edges are pulled toward the directions opposite to each other and, then, the film is energized, said electrophoretic apparatus being thereby arranged so that the film is kept free from slack when it is being energized.

Another object of the present invention is to provide an electrophoretic apparatus for an automatic electrophoretic system arranged so that the film easily parts from the filter paper retainers, after completion of energization, by using rod-like members as the filter paper retainers.

DETAILED DESCRIPTION OF THE PREFERRED EMBODIMENT

Figure 1:
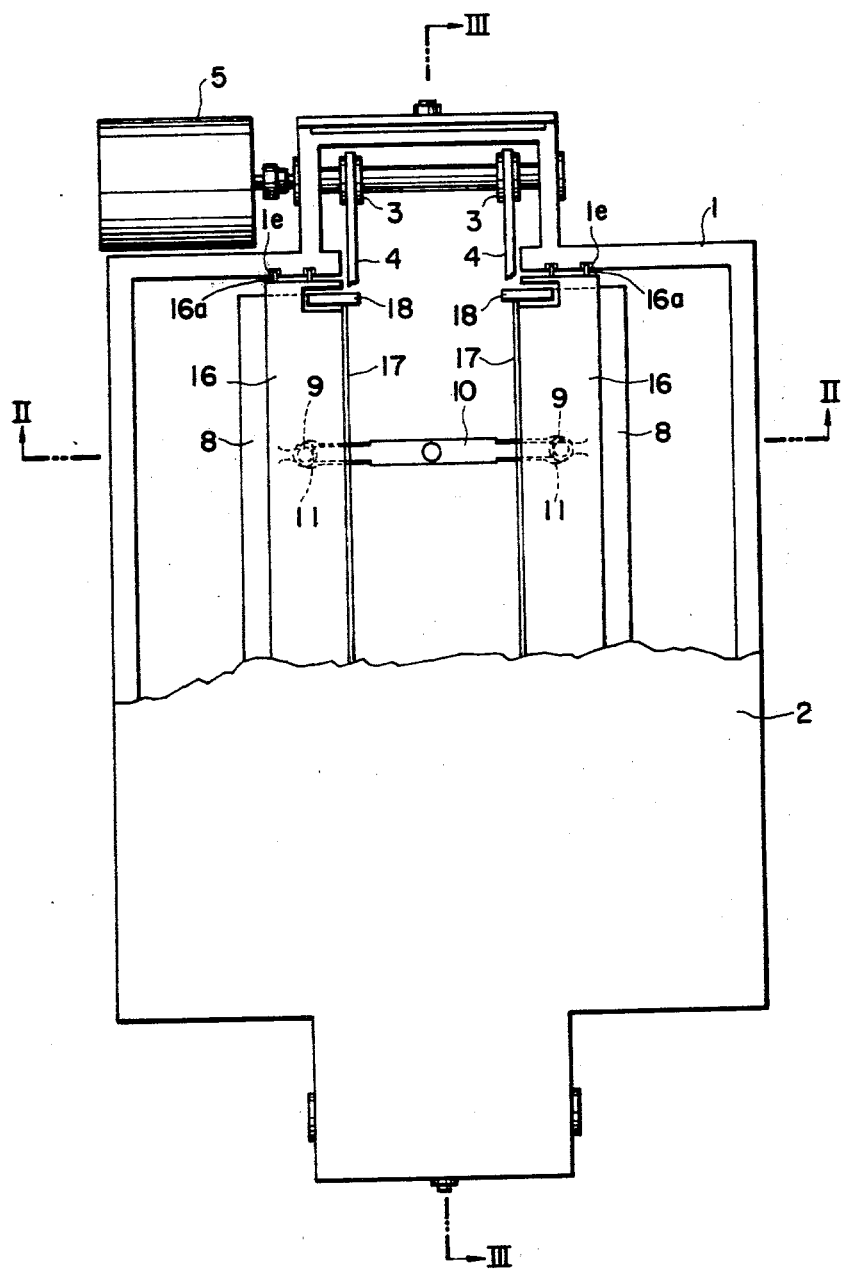
FIG. 1 shows a plan view of known electrophoretic apparatus.
Figure 2:
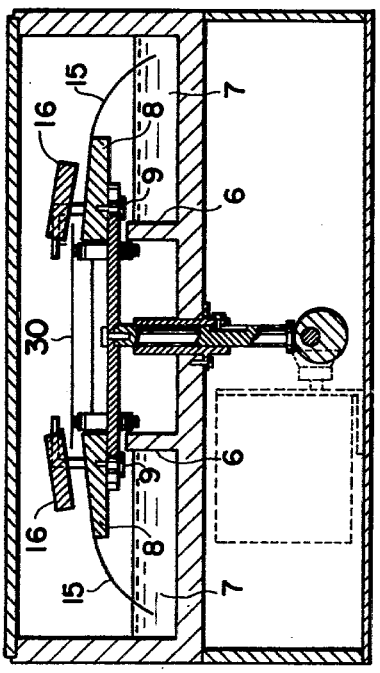
FIG. 2 shows a sectional view taken along the line II—II in FIG. 1.
Figure 3:
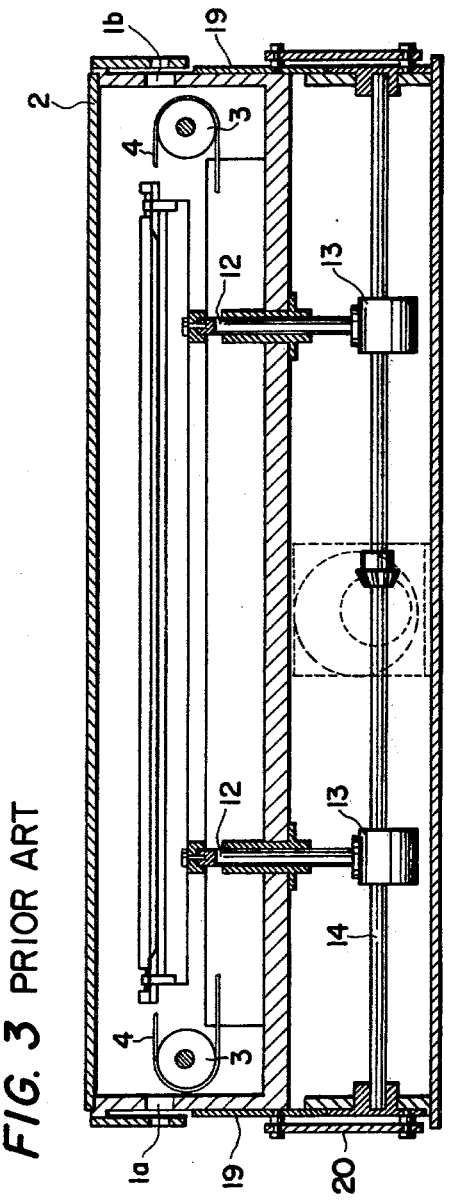
FIG. 3 shows a sectional view taken along the line III—III in FIG. 1.
Figure 4:
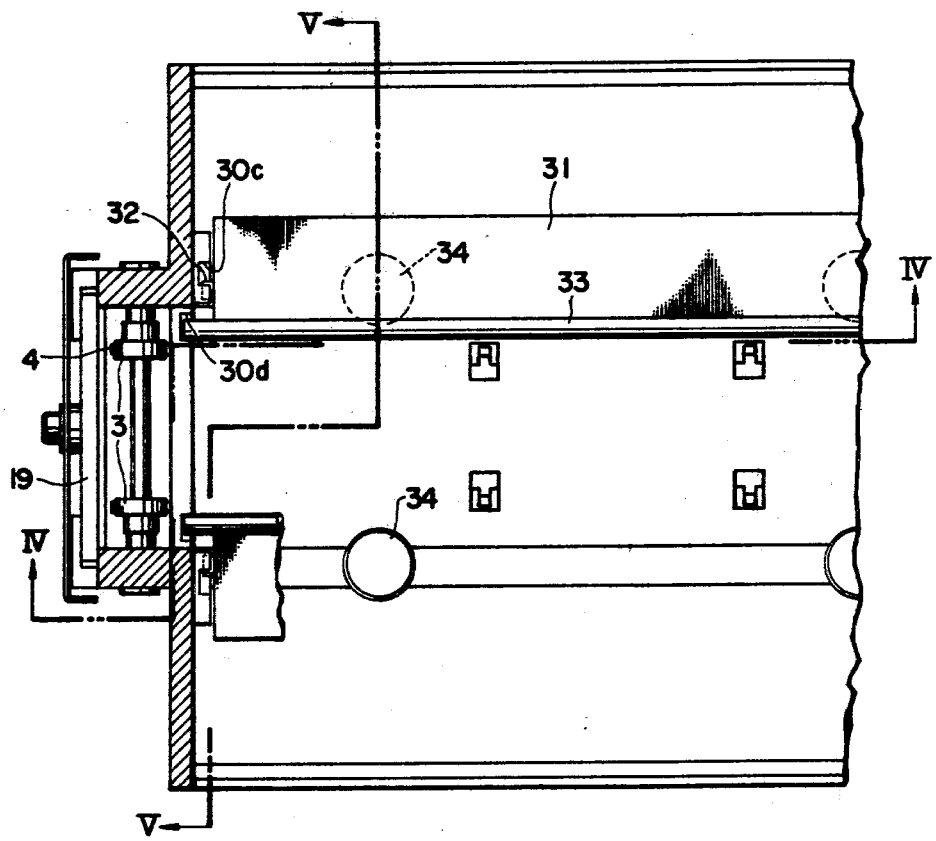
FIG. 4 shows a partially broken plan view of electrophoretic apparatus according to the present invention.
Figure 5:
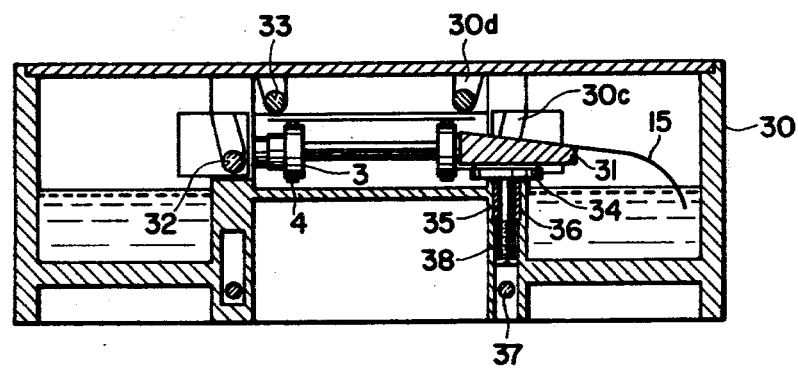
FIG. 5 shows a sectional view taken along the line V—V in FIG. 4.
Figure 6:
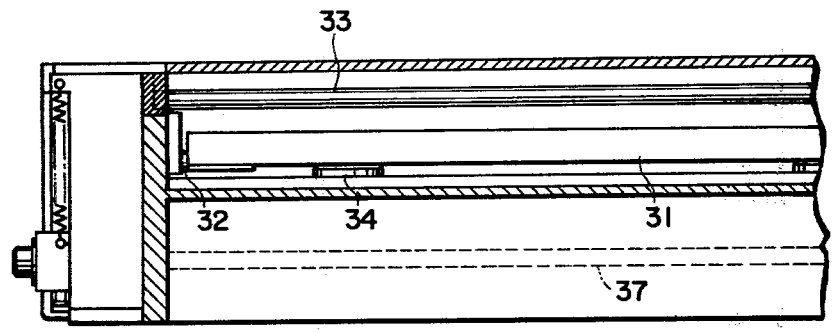
FIG. 6 shows a sectional view taken along the line VI—VI in FIG. 4.

Now, the concrete content of electrophoretic apparatus according to the present invention is described below based on the embodiment shown on the drawings. In FIGS. 4 through 6, numeral 31 designates a pair of filter paper supports made of such material as glass and having a shape approximately the same as the filter paper supports 8 of the known apparatus. At both ends of each filter paper support 31, guide pins 32 are fixed. On the inner surfaces at both ends of main body 30 of electrophoretic apparatus, grooves 30c are formed in the shape as shown in the left portion in FIG. 5. By inserting the guide pins 32 into those grooves 30c, the filter paper supports 31 are located in the pre-determined positions in the main body 1, Numeral 33 designates a pair of filter paper retainers made of such material as glass and having a rod-like shape. Each filter paper retainer 33 is held in position by inserting its both ends into grooves 30d formed on the inner surfaces at both ends of main body 30. Numeral 34 designates rests for filter paper supports fixed to supporting rods 35. The supporting rods 35 are arranged in sleeves 36 so that the supporting rods can be moved upward and downward. As the filter paper supports 31 are placed on the rests 34, the filter paper supports 31 can slide in the direction at a right angle to the longitudinal direction of film when the supporting rods 35 are moved upward and downward. Numeral 37 designates a pair of operating shafts arranged so that they can be moved upward and downward in order to move the filter paper supports 31 upward and downward through the supporting rods 35 and rests 34. Numeral 38 designates springs. As composition of the other component parts is substantially same as the known apparatus shown in FIGS. 1 through 3, the same numerals as the known apparatus are given in the figures to those component parts which are substantially same and explanation is omitted here.

Now, operation of the above-mentioned electrophoretic apparatus is described below. At first, when the operating shafts 37 are moved downward, the doors 19 at the entrance and exit which are mounted at both ends of operating shafts 37 are opened and, at the same time, the filter paper supports 31 move downward. In this state, the film to which blood serum specimens are applied is inserted through the entrance and is fed into the apparatus by means of endless belts 4. Then, movement of film is stopped at the pre-determined position by stopping the endless belts. When the operating shafts 37 are moved upward in the above-mentioned state, the filter paper supports 31 are moved upward and the film is parted from the endless belts 4. When the operating shafts 37 are further moved upward to push the filter paper supports 31 upward, edges of film are held between the filter paper supports 31 and filter paper retainers 33 and the film is moved upward in that state. When the filter paper supports 31 are still moved upward, they are moved obliquely upward parting from each other due to the fact that the grooves 30c, which are formed on the inner surfaces at both ends of main body 30, have the shapes as shown in FIG. 5. Consequently, each edge of film is pulled outward in the state that it is held between the corresponding filter paper support 31 and filter paper retainer 33. As a result, the middle portion of film does not hang slack. When the film is energized in that state, the film is kept free from slack when it is being energized and, therefore, it is possible to obtain favourable fractionated patterns. When the operating shafts 37 are moved downward after completion of energization, the filter paper supports 31 and filter paper retainers 33 move donward by holding the film and filter paper between them. In the course of downward movement, the filter paper retainers 33 reach the lower ends of grooves 30d and stop the downward movement there. Consequently, only the filter paper supports 31 further move downward and the film is placed again on the endless belts parting from the filter paper retainers 33. The filter paper supports further move downward in obliquely inward direction and return to the original positions. Then, the endless belts 4 are started again and the film is moved outside the apparatus.

Figure 7:
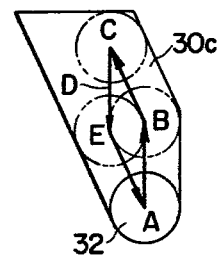
FIG. 7 shows a diagram illustrating the movement of filter paper support.

FIG. 7 shows a diagram illustrating the movement of filter paper support. Though FIG. 7 shows the movement of filter paper support on the left side only, the movement of filter paper support on the right side is symmetrical with the above. When the supporting rod 35 moves upward, the filter paper support 31 and filter paper 15 are moved upward through the rests 34 and the filter paper support 31 contacts the filter paper retainer 33. At that time, the guide pins 32 move from the point A to the point B in FIG. 7. After that, each guide pin 32 is moved from the point B to the point C along one oblique side surface of groove 30c and, consequently, the filter paper support 31 moves obliquely upward. By this movement, the filter paper retainer 33 is also moved obliquely upward along the oblique side surface of groove 30d. At that time, the film moves upward in the state that its each edge is pulled outward. After energization at the point C, the filter paper support 31 moves downward, parts from the filter paper retainer at a position near the point D in the course of downward movement and, then, reaches the point E. After the above, each guide pin 32 moves from the point E to the point A along the other side surface of groove 30c. Therefore, the filter paper support 31 moves obliquely downward and returns to the original position.

Figure 8:
FIG. 8 shows a perspective view illustrating another example of filter paper retainer.

Moreover, due to the fact that the filter paper supports have flat surfaces and filter paper retainers have the rod-like shape, the film reliably contacts the filter paper sheets by the whole straight lines when the edges of film are held between the filter paper supports and filter paper retainers by upward movement of filter paper supports. Besides, when the filter paper supports are moved downward, the film easily parts from the rod-like filter paper retainers. Therefore, it is not necessary to provide the wires which are used in the known apparatus. The shape of filter paper retainers is not limited to the round rod-like shape. It is also possible to use such rods having triangular or polygonal cross section by arranging so that one edge or corner of each rod comes to the bottom. Besides, it is also possible to use round rods by winding a wire to each rod as shown in FIG. 8 and, then, covering it with plastic film for the purpose of insulation.

Alternatively, it is also possible to provide pins at both ends of each filter paper retainer and to insert those pins into the grooves of main body instead of directly inserting both ends of each filter paper retainer into the above-mentioned grooves.

As explained in the above, in case of the electrophoretic apparatus according to the present invention, the filter paper supports move as described before. Therefore, even if the middle portion of film placed on the endless belts hangs slack, both edges of film are pulled after the film parts from the endless belts and, consequently, the film becomes free from slack. As the film is energized in that state, it is possible to obtain favourable fractionated patterns.

Moreover, in case of the electrophoretic apparatus according to the present invention, the film is reliably put to close contact with the filter paper sheets and, therefore, it is possible to obtain favourable fractionated patterns also from this view point. Moreover, after energization, the film easily parts from the filter paper retainers. Therefore, it is not necessary to provide the means for parting the film from the filter paper retainers and construction of the apparatus becomes simple.

We claim:

1. An electrophoretic apparatus comprising a pair of endless belts, a pair of long board-like filter paper supports arranged on the outer sides of said pair of endless belts, a pair of filter paper retainers arranged above said pair of filter paper supports, buffer solution troughs arranged on the outer sides of said pair of filter paper supports, and two sheets of filter paper, each sheet of filter paper being arranged that its one edge portion rests on the top surface of one of said filter paper supports and the other edge portion is arranged in one of said buffer solution troughs and dipped into buffer solution, said electrophoretic apparatus is arranged that, after a film is conveyed into said apparatus by means of said endless belts, edge portions of said film are held between said filter paper supports and filter paper retainers by moving said filter paper supports upward, the film is thereby moved upward to part from said endless belts, said filter paper supports are then moved obliquely upward so that they part from each other in order to make the film free from slack and, then, the film is energized through said sheets of filter paper in the state that the film is free from slack.

2. An electrophoretic apparatus according to claim 1 further comprising a main body accommodating said endless belts, said filter paper supports, said filter paper retainers and said buffer solution troughs, pins provided to each of said filter paper supports, pins provided to each of said filter paper retainers, and a vertical movement mechanism for moving said filter paper supports upward and downward, said main body having first grooves formed on inner surfaces of said main body for the purpose of supporting said filter paper supports by inserting said pins provided to said filter paper supports into said first grooves and formed in such shape that lower portions of said first grooves are vertical while upper portions of said first grooves are inclined toward directions opposite to each other so that the distance between upper portions of said first grooves becomes larger toward the top portions, said main body further having second grooves also formed on inner surfaces of said main body for the purpose of supporting said filter paper retainers by inserting said pins provided to said filter paper retainers into said second grooves.

3. An electrophoretic apparatus according to claim 1, in which said filter paper retainers are made of rod-like members.

4. An electrophoretic apparatus according to claim 3, in which said filter paper retainers have polygonal cross sections.

5. An electrophoretic apparatus according to claim 3, in which each of said filter paper retainers comprises a spirally wound wire and plastic film covering said filter paper retainer and wire.

6. An electrophoretic apparatus according to claim 2 further comprising doors respectively arranged at a film entrance and film exit formed in said main body, said doors being arranged to open and close in combined operation with said vertical movement mechanism.

* * * * *